United States Patent [19]

Barbera Alacreu

[11] Patent Number: 5,649,925
[45] Date of Patent: Jul. 22, 1997

[54] SYSTEM FOR SETTING CERVICAL VERTEBRAE FROM BEHIND

[75] Inventor: José Vicente Barbera Alacreu, Juan Martorell 1, bajo, 46010 Valencia, Spain

[73] Assignees: Jose Vicente Barbera Alacreu; Jose J. Aparici Marin; Jose Ramon Bilbao Ortiz De Zarate, all of Valencia, Spain

[21] Appl. No.: 440,142

[22] Filed: May 12, 1995

[30] Foreign Application Priority Data

May 13, 1994 [ES] Spain ................................ 9401028

[51] Int. Cl.$^6$ .................................................. A61B 17/70
[52] U.S. Cl. ........................ 606/61; 606/72; 606/103
[58] Field of Search ............................. 606/61, 53, 54, 606/57, 60, 72, 74, 103

[56] References Cited

U.S. PATENT DOCUMENTS 1,276,117  8/1918  Riebe .................................. 464/171
1,279,803  9/1918  Watson ................................ 248/160
3,858,578  1/1975  Milo .

FOREIGN PATENT DOCUMENTS

0-167345  1/1986  European Pat. Off. .
0522040   3/1921  France .
2-697428  5/1994  France .
1958429   11/1969 Germany .

Primary Examiner—Michael Buiz
Assistant Examiner—David O. Reip
Attorney, Agent, or Firm—Birch, Stewart, Kolasch & Birch, LLP

[57] ABSTRACT

A system for setting cervical vertebrae from behind includes hooks (10) and plates (12) used together with a number of jointed segments or cylinders (1) crossed longitudinally and vertically by a web (4) housing a connecting wire (8) that can be tightened with a tightening device, and locked by a screw (7) lying crosswise to each segment (1). The system can be used to join all the required levels. Neither the point of insertion of the screws nor the position of the hooks are predetermined. This system can be used after laminectomy.

14 Claims, 7 Drawing Sheets

SYSTEM FOR SETTING CERVICAL VERTEBRAE FROM BEHIND

FIELD OF THE INVENTION

The present Invention relates to a system for setting cervical vertebrae from behind providing, in addition to the function for which it has been conceived, a number of advantages that shall be explained hereinafter and others that are inherent in its layout and construction.

BACKGROUND OF THE INVENTION

Several systems designed specifically to set the cervical column from behind are currently known. The conventional systems, being a part of the prior art, could be divided into the five types listed below:

Wires passing through holes made on the rear arch of each vertebra to be fixed, that are then knotted to form a lacing that joins the vertebrae to one another. It is inconvenient in that the resulting set is not sufficiently solid and, if the wires are passed beneath the laminae, manipulation can prove dangerous.

Longitudinal bars joined to the vertebrae by means of wires passing beneath the rear arch laminae and then knotted around the bar. It is inconvenient in that the wires must pass beneath the laminae and this is dangerous.

Hooks catching hold of the vertebral laminae and then being joined to each other by bars or screws. The Halifax system is inconvenient in that it is only useful to join two levels. The bar and hook systems can only catch hold of the two end vertebrae and not the intermediate vertebrae. They cannot be used after laminectomy.

Plates fixed to the vertebrae with screws that catch hold of the articular mass of each vertebra. It is inconvenient in that the plates, being rigid, predetermined and conditions the place at which screws are inserted.

The Magerl system combines the previous two systems and has a sublaminar hook and a plate, joined to the hook, that is screwed to one or two articular masses. It is inconvenient in that being a rigid part, the position of the screws is predetermined and is further only useful to join two or three levels.

SUMMARY OF THE INVENTION

The applicant for the present Invention has used his experience in the medical science subject hereof to design a new system for setting the cervical vertebrae from behind which conveniently overcomes the drawbacks that are usually found in prior art methods, succinctly described in the above section, now using hooks and plates and a number of jointed segments or cylinders crossed longitudinally and vertically together to establish a web housing a connecting wire that can be tightened and locked by a screw lying crosswise to the segment, which entails a number of advantages:

Possibility of being used to join all the required levels.

Because it is jointed, neither the point of insertion of the screws nor the position of the hooks are predetermined, eliminating risks and expediting the placement and adaptation of the system to the morphology of the column.

Having screws and hooks, it can also be used after laminectomy.

The System of the present Invention affords the foregoing advantages, in addition to others that may be easily inferred from the embodiment described in detail hereinafter to expedite the understanding of the characteristics set out before, contemporaneously revealing a number of details, this specification having attached to such end a number of drawings showing, for illustrative and non-limitative purposes, a practical embodiment of its object.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF AN EMBODIMENT OF THE INVENTION

As shown in the drawings, the system for setting cervical vertebrae subject hereof, and in accordance with an embodiment thereof, comprises several distinct elements:

The first group of elements comprises different parts, that we shall call segments or cylinders.

Each of the segments is a solid metal cylinder -1- whose two ends are different.

The top end is a hemisphere -2- having a diameter that is 0.5 millimeters shorter than the diameter of the cylinder.

The lower end is scooped and forms a likewise hemispherical cavity -3- having an internal diameter that is 0.5 millimeters shorter than the diameter of the cylinder.

The reason for having this shape and these dimensions at the ends is that the top protruding end of a cylinder can be precisely coupled to and turn within the lower scooped end of another cylinder arranged above the same.

The whole cylinder is longitudinally crossed vertically by a hollow cylindrical path -4- having a 2 millimeter calibre, that opens at the top and bottom ends. This path we shall refer to as a cylinder web.

At the top end, surrounding the top opening of the inner duct, there are four small holes -5- arranged at the ends of a cross whose lines are each 4 millimeters long. The holes are for the wire -8- plate -9- to be fitted.

Halfway up the stem of the cylinder there is a threaded bore -6- with a 1.5 millimeter calibre, reaching the internal duct -4- or cylinder web. This bore shall house a small screw -7- whose blunt point shall, when fully screwed in, reach up to the opposite wall of the internal vertical duct of the cylinder. This is the screw that locks the wire -8-.

Figure 1:
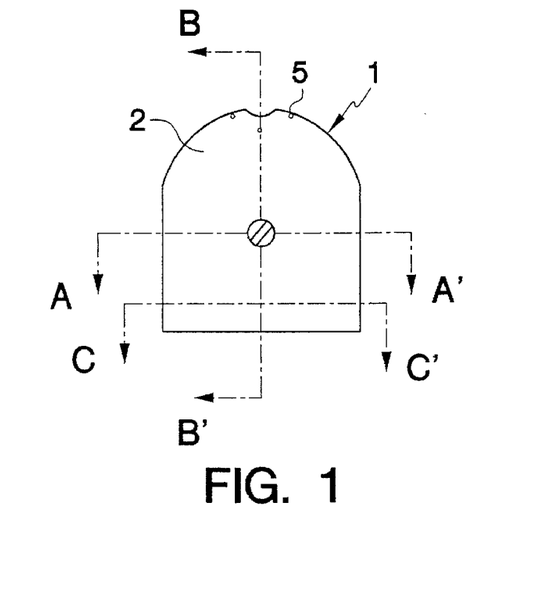
FIGS. 1 and 2 show a side elevation view of two segments or cylinders, being respectively large and small.

The cylinders are two in size:

Large, as in FIG. 1, being 8 millimeters high, measured from the pole of the top hemisphere down to the perimeter of the hollow lower base, and being 5 millimeters in diameter.

Figure 2:
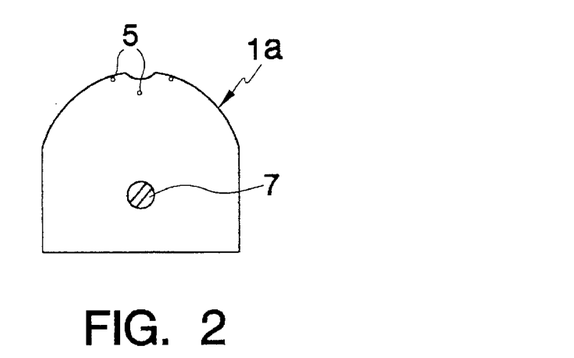
Figure 3:
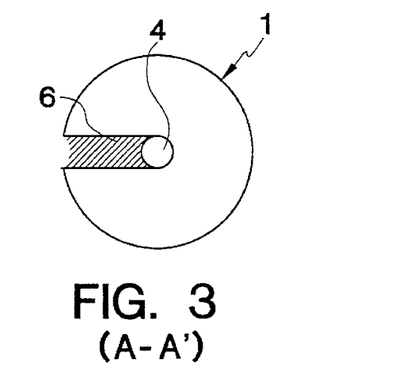
FIGS. 3, 4 and 5 are cross-sections of the said elements, viewed along A–A', B–B' and C–C'.
Figure 4:
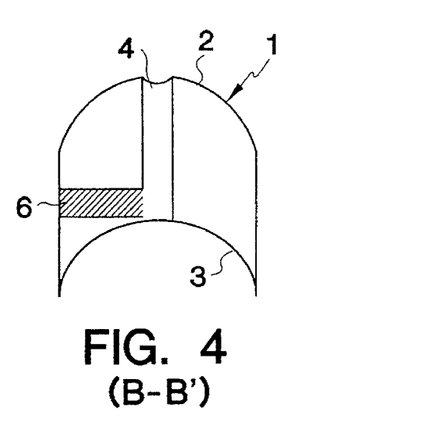
Figure 5:
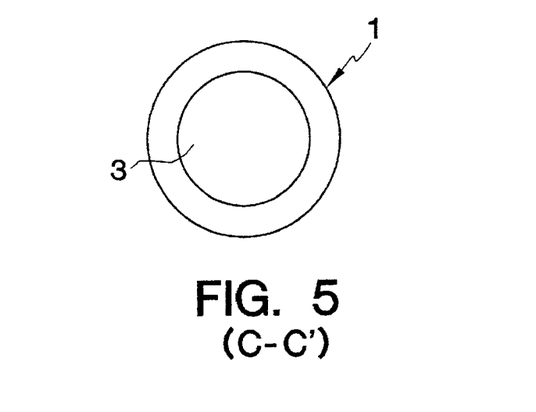

Small 1a, as in FIG. 2, being 4 millimeters high and 5 millimeters in diameter.

The large cylinders are divided into four types:

SIMPLE: Comprising a simple cylinder as described in FIGS. 1 to 5.

Figure 6:
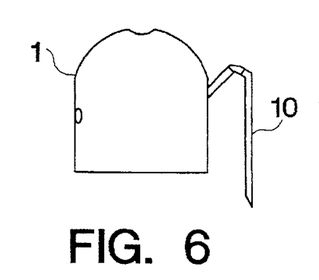
FIGS. 6, 7 and 8 show side elevation views of a type of cylinder having a downward hook.
Figure 7:
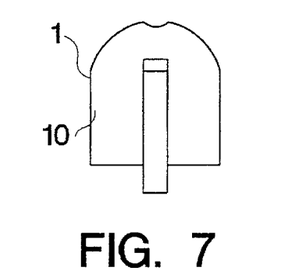
Figure 8:
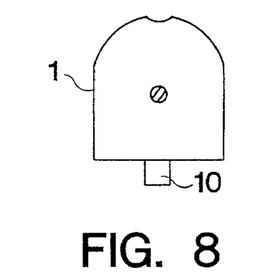

WITH DOWNWARD HOOK: This is a "simple" cylinder with a hook -10- projecting from one of its sides. This hook shall comprise a 5 millimeter wide sheet projecting from the top half of the cylinder body, at an upwardly open 45° angle to the longitudinal axis of the cylinder. The sheet then bends down until its final portion is parallel to the longitudinal axis of the cylinder. In this type, the wire locking screw bore lies at the side of the cylinder being diametrically opposite the projection of the hook, as shown in FIGS. 6 to 8.

Figure 9:
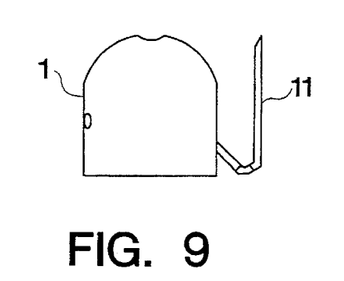
FIGS. 9, 10 and 11 show side elevation views of another type of cylinder having an upward hook.
Figure 10:
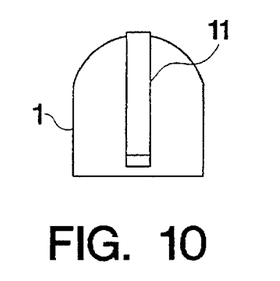
Figure 11:
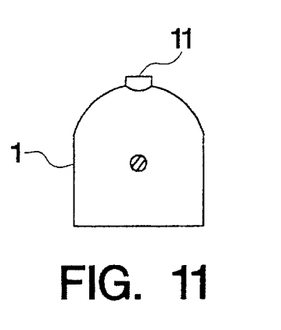

WITH UPWARD HOOK: This is similar to the above, though in this case the hook -11- projects from the lower half of the cylinder at a downwardly open 45° angle and the sheet then bends up. In this type, the wire locking screw bore lies at the side of the cylinder being diametrically opposite the projection of the hook, as shown in FIGS. 9 to 11.

Figure 12:
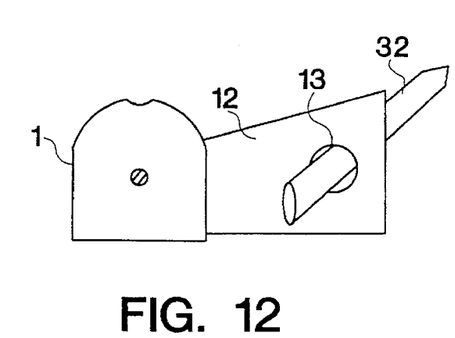
FIGS. 12, 13 and 14 show side elevation views of a third type of cylinder having a screw plate.
Figure 13:
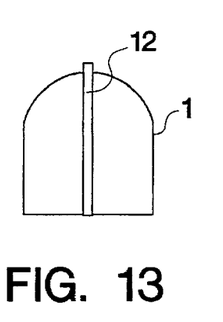
Figure 14:
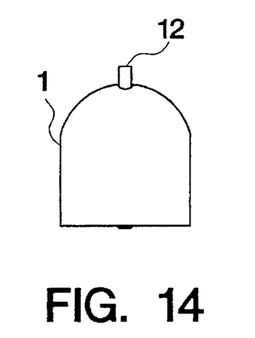

WITH ARTICULAR SCREW PLATE: A trapezoidal vertical plate -12- projects from the cylinder body at the major axis plane of the cylinder, extending sideways for 15 millimeters. The shorter side of the plate has the same length as the cylinder stem. The longer side of the plate measures 8 millimeters. The plate is crossed at 2 millimeters from its free end, its longer end, by a hole -13- having a diameter of 3 millimeters. In this type, two bores are provided for the wire locking screw, lying on both the front and the rear faces of the cylinder, relative to the plate.

There are two types of small cylinders:

SIMPLE: Carrying no hooks or plate, as in FIG. 2.

Figure 16:
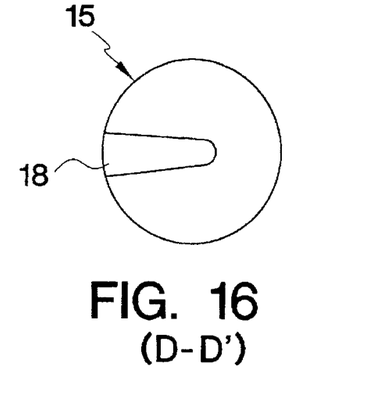
FIGS. 16 and 17 are cross-sections of the cylinder of the previous figure, seen along D–D' and E–E'.
Figure 17:
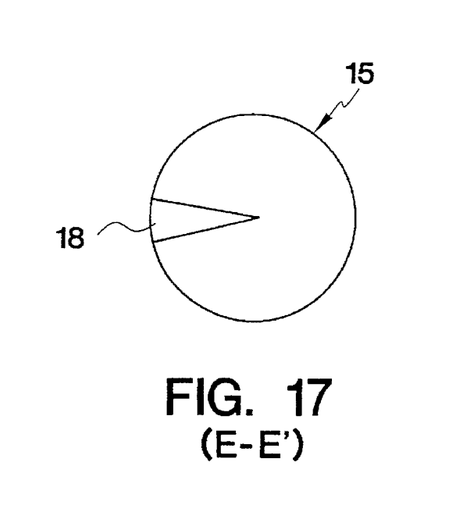
Figure 18:
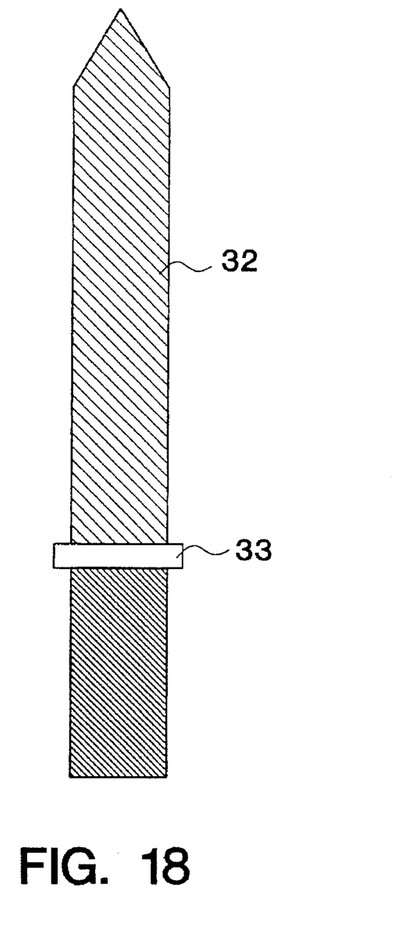
FIG. 18 shows the articular screw.

CLOSING CYLINDER: this cylinder is numbered -15- and has a particular morphology. Its lower end is not scooped, and is flat instead as at -16-. The stem -17- of the cylinder has a dihedral notch -18- along its length, leading towards the central axis. It carries no locking screw. The web, which opens at the top end, continues at the height of the cylindrical stem with the inner angle of the notch as in FIGS. 15 to 17.

Figure 19:
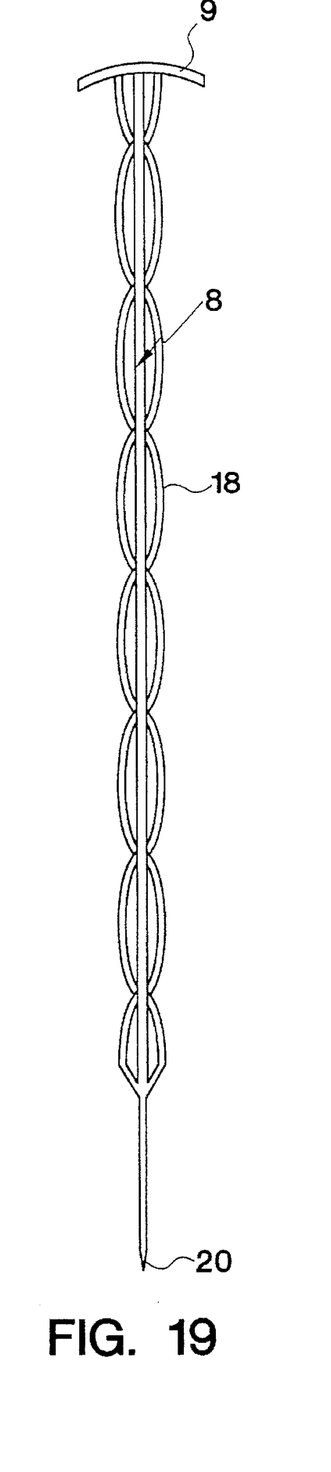
FIGS. 19 and 20 are the internal wire and a close view of the wire plate.
Figure 20:
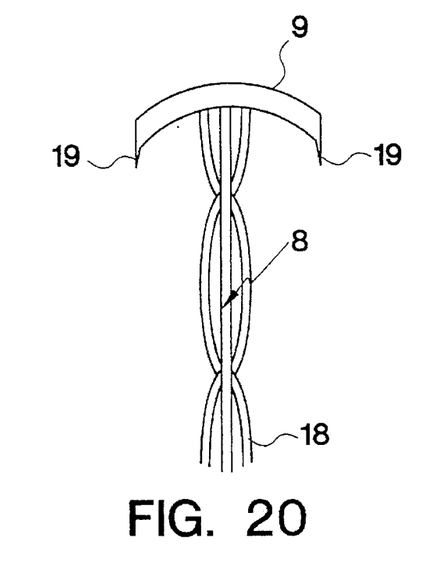

The second group of elements comprises the internal wire -8- and its components:

The components are:

A braided metal wire -18- being 40 centimeters long and 1.5 millimeters thick, being therefore able to pass freely through the hollow web of the segments.

At one end the wire is fixed to a circular plate -9- having a diameter of 4 millimeters, and shaped as a spherical shell, the surface of which adjusts to the top end surface of the cylinder. This is the wire plate. Four spikes -19- being each 1 millimeter long, project from the ends of two perpendicular diameters of this plate, which shall be housed in the four bores -5- at the top end of the cylinder -1-.

The other end of the wire ends in a point -20- that allows the same to be easily threaded through the web of the segments. This is the wire point.

Figure 21:
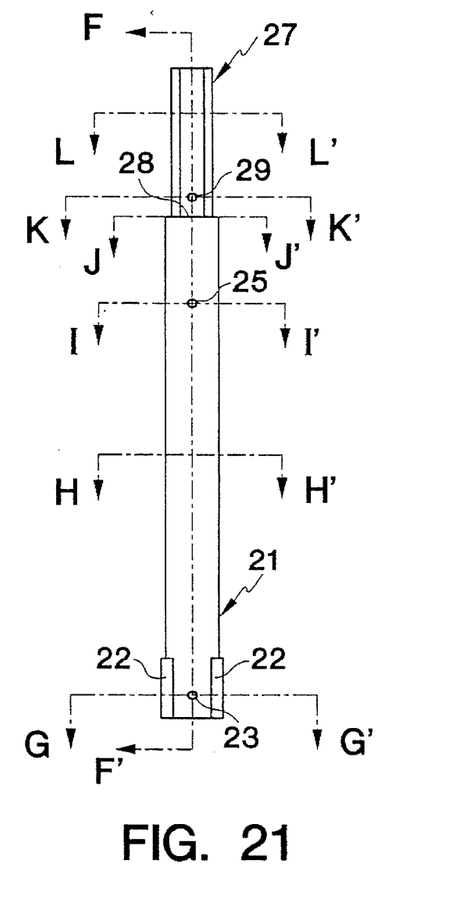
FIGS. 21, 22 and 23a–23c show the wire tightening wrench, seen separately as a front elevation of the top and lower part, a side elevation thereof and a plan view of the top part.

The third element is the wire tightening wrench.

Figure 22:
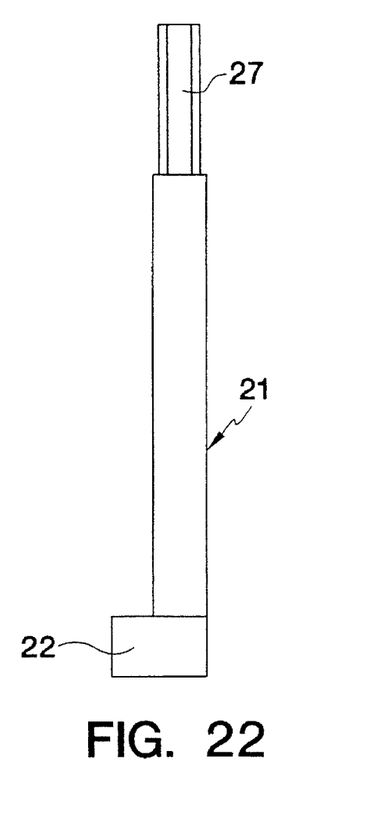
Figure 23A:
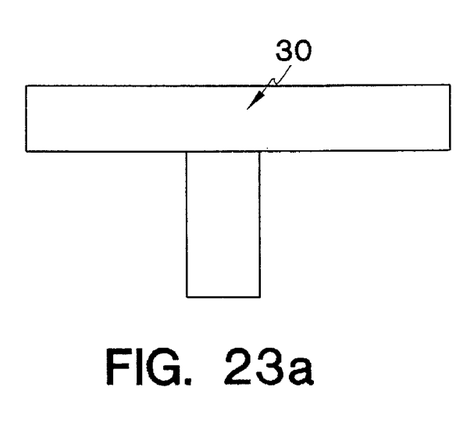
Figure 23B:
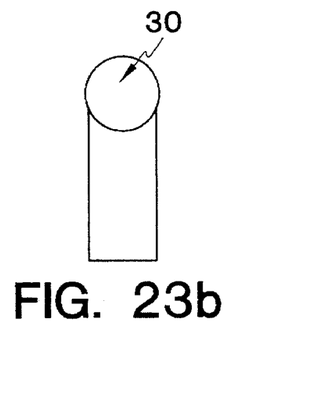
Figure 23C:
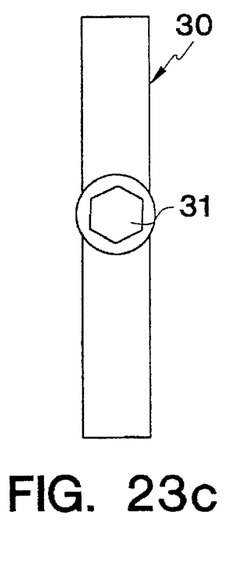

Such comprises three parts, as in FIGS. 21 to 23. The lower part is a metal cylinder being 20 centimeters long and 1 centimeter in diameter. Its lower end has two curved sheets -22- being sized so as to be able to firmly couple between the same the closing cylinder.

Figure 24:
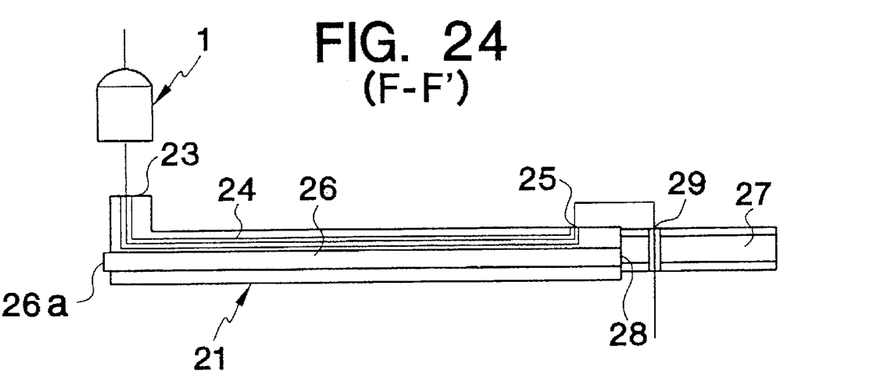
FIG. 24 is a longitudinal section of the lower part of the wire tightening wrench, seen along F–F'.
Figure 25:
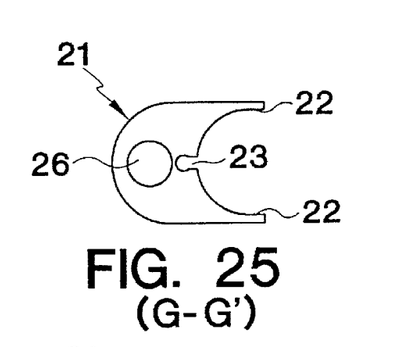
FIGS. 25, 26, 27, 28, 29 and 30 are the various sections of the lower part of the wire tightening wrench, seen along G–G', H–H', I–I', J–J', K–K' and L–L'.
Figure 26:
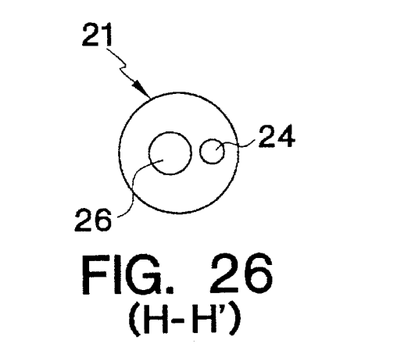
Figure 27:
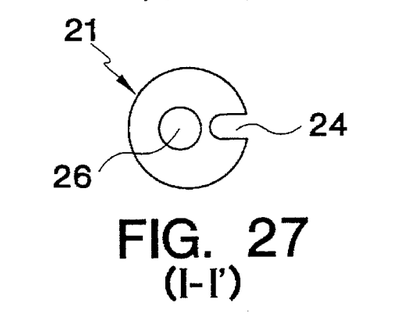
Figure 28:
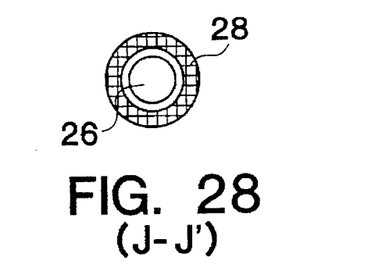
Figure 29:
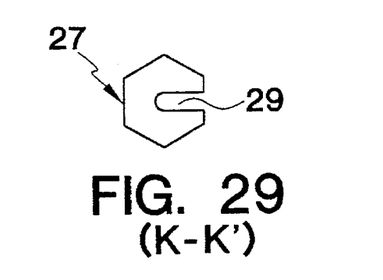
Figure 30:
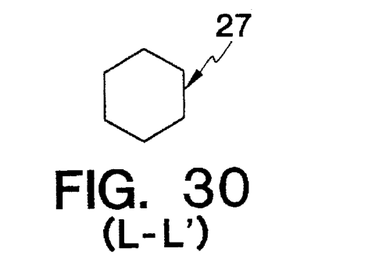

A 2 millimeter bore -23- is provided on the surface of the cylinder at the midpoint between these two sheets which extends upwards as at -24- along the stem of the cylinder to again surface at -25-, 2 centimeters from the top end.

The surface of the top end has a cylindrical scoop that extends along the central axis down to the lower end. This cavity houses the stem -26- of the top part -27-.

The circular perimeter of the top surface is a cog-wheel -28- with triangular rectangular cogs.

The top part -27- is a hexagonal prism with a major diameter of 6 millimeters and a length of 3 centimeters. A 2 millimeter bore -29- appears at a distance of 5 millimeters from its lower end, extending upwards inside the prism to surface again on the same face, 1 centimeter higher. A cylindrical stem, -26- projects from the lower end of the prism, which fits in the cavity provided therefor in the lower part, crossing its full length, leaving through the lower end of such part, as at -26a-. At its outlet from the lower end of the lower part, the stem has a small boss that prevents vertical movement, thereby permanently fixing both parts.

The lower end of the top part is a cog-wheel, with triangular rectangular cogs arranged inversely to the cogs on the lower part.

A T shaped torque wrench -30- with a hexagonal pitch -31- adapting to the prism -27- on the top part and allowing to same to turn about the lower part clockwise. The return motion is prevented by the cog-wheels on both abutting parts.

After exposing the rear arches of the vertebral segments that are to be merged, a decision is made as to the type of setting elements that are to be used for each level, hooks or screws, and the respective distances at which these elements shall have to be positioned are calculated.

At the levels where screws -32- are to be used, these are placed directly on the articular masses, introducing the same to the limit and without any limitations as to their position.

Figure 31:
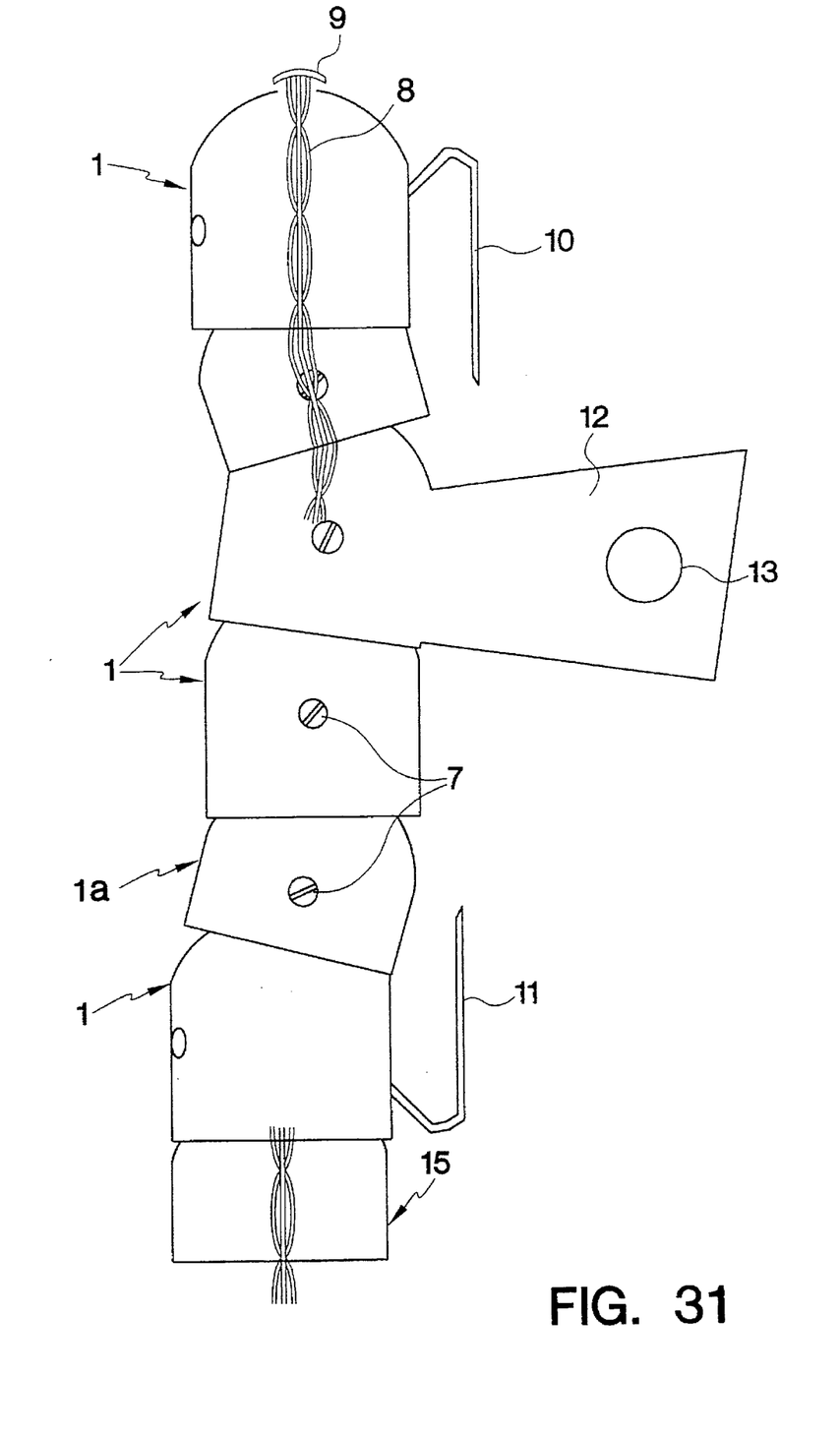
FIG. 31 shows an embodiment of the assembled, stiffened and coupled system with the incurvations imposed by the setting elements.

The various cylinders having the required setting elements (upward facing hook -11-, downward facing hook -10-, screw plate -12-) and the simple cylinders of different sizes are strung in the braided wire -8-18-. With the various sizes of simple cylinders 1, 1a the assembly shall be adjusted to the anatomic demands required by the vertebral morphology and size.

The hooks are placed on the laminae and for the levels in which a screw -32- has been inserted, a cylinder and a plate -12- are placed. The projecting stem -33- of the screw is inserted through the bore in the plate -12- and the nut attaching the plate to the screw is then placed. As previously stated, the distance between setting elements is covered with like elements.

The last element strung in the wire is a closing cylinder -15-.

After the system is all assembled, the central wire -8- is tightened using the appropriate wrench described in the apparatus section, and the system is thereby stiffened, adjusting to the incurvations imposed by the setting elements. Coupling is achieved due to the turning capacity that the hemispherical arrangement at the top and lower ends of each cylinder provides.

When the central wire is tightened to the limit, before removing the tightening wrench, the final position is consolidated by screwing the small screws -7- with which each cylinder is provided, compressing the wire in the central duct, preventing it from sliding.

5 The tightening wrench is removed and forceps are used to tighten the closing cylinder -15- to the wire, solidly fixing the whole system.

The closing cylinder -15- is coupled between the sheets -22- of the bottom end of the wrench -21-.

Figure 15:
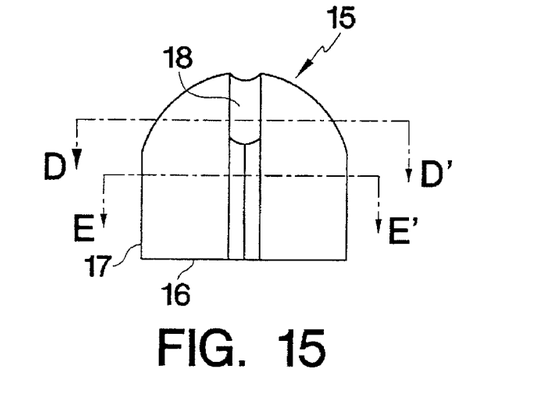
FIG. 15 illustrates a side elevation view of a closing cylinder.

The tightening wire is placed in the dihedral angle -18- of the closing cylinder and is then inserted through the lower bore of the lower part until it leaves through the top bore.

The wire is then inserted through the lower bore of the top part until it leaves through the top bore.

At this point, the torque wrench is used to turn the top part about the lower part, in such a way that the free end of the wire is wound around the prism and is tightened until the torque wrench stops turning.

The tension applied to the wire is preserved because the two cog-wheels at the top and bottom ends of the two parts prevent a turn in the direction opposite the direction in which force is applied.

With the wrench in position, the locking screws in each cylinder are gradually tightened, starting with the top cylinder and moving down towards the bottom cylinder.

After tightening each locking screw it is found that the torque wrench cannot turn, in other words, it is found that the wire has lost no tightness.

Once all the locking screws are tightened, the tightening wrench is removed and suitable forceps are used to tighten the closing cylinder -15- in order for the dihedral angle -18- to close upon the wire -8-18- preventing it from slipping or becoming loose.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A system for setting cervical vertebrae from behind, said system comprising:

at least two cylindrical members, said cylindrical members having two distinct lengths, long and short, and having a cylindrical body, a convex hemisperically shaped upper end, and a corresponding concave hemisperically shaped lower end, allowing said members to stack end-to-end such that the said convex upper end of one said member precisely couples into and may articulate in said concave lower end of another said member;

a braided wire member for connecting together said cylindrical members to form a structural assembly;

a wire tightening tool for tightening said wire in said cylindrical members to stiffen said assembly; and a locking member provided in each of said cylindrical members for securing said wire to a respective individual one of said cylindrical members.

2. The system for setting cervical vertebrae from behind as set forth in claim 1, and further comprising said cylindrical members as having an axial bore through hole parallel to and concentric with the longitudinal axis of said cylindrical body such that said axial bore enters at the center to said convex upper end and exits at the center of said concave lower end, said members further having four holes in said upper end arranged 90 degrees from each other, equidistant from and concentric with said axial bore, said member further having a hole drilled through the radius of said cylindrical body, placed at the midpoint of said body and perpendicular to said axial bore, said hole reaching said axial bore and being threaded to receive a set screw for clamping said member to said braided wire member in said axial bore.

3. The system for setting cervical vertebrae from behind as set forth in claim 1, wherein said long cylindrical member is twice a length of said short cylindrical member.

4. The system for setting cervical vertebrae from behind as set forth in claim 3, wherein said long cylindrical member is 8 millimeters in length and 5 millimeters in diameter, and said short cylindrical member is 4 millimeters in length and 5 millimeters in diameter.

5. The system for setting cervical vertebrae from behind as set forth in claim 1, wherein said long cylindrical member includes a hook extending from a side of said body and directed downwardly in a direction toward said lower end of said body.

6. The system for setting cervical vertebrae from behind as set forth in claim 5, wherein said hook includes a first portion extending outwardly from said body at approximately 45° to a longitudinal axis of said cylindrical body, and a second substantially straight portion extending substantially parallel to the longitudinal axis of said cylindrical body.

7. The system for setting cervical vertebrae from behind as set forth in claim 1, wherein said long cylindrical member includes a hook extending from a side of said body and directed upwardly in a direction toward said upper end of said body.

8. The system for setting cervical vertebrae from behind as set forth in claim 7, wherein said hook includes a first portion extending outwardly from said body at approximately 45° to a longitudinal axis of said cylindrical body, and a second substantially straight portion extending substantially parallel to the longitudinal axis of said cylindrical body.

9. The system for setting cervical vertebrae from behind as set forth in claim 1, wherein said long cylindrical member includes a plate extending from a side of said body and directed outwardly in a direction away from said side of said body.

10. The system for setting cervical vertebrae from behind as set forth in claim 9, wherein said plate comprises a trapezoidal plate oriented vertically with respect to said cylindrical body, said plate including an aperture for receiving an articular screw therein.

11. The system for setting cervical vertebrae from behind as set forth in claim 1, and further including a short cylindrical member having a flat lower end and a dihedral notch in a sidewall thereof for performing a structural assembly closing function.

12. The system for setting cervical vertebrae from behind as set forth in claim 1, wherein said braided wire member includes a circular hemispherical plate attached to a first end thereof, and a pointed member located at a second end thereof.

13. The system for setting cervical vertebrae from behind as set forth in claim 12, wherein said plate includes a plurality of spikes extending therefrom for engagement with corresponding holes in the upper end of one of said cylindrical members.

14. The system for setting cervical vertebrae from behind as set forth in claim 1, wherein said wire tightening tool includes a cylindrical rod member having a first end and a second end, said first end having a pair of scoop members for engaging one of said cylindrical members, said second end having a projection for engagement with a T-shaped wrench having a socket corresponding to a shape of said projection.

* * * * *